United States Patent
Sato et al.

(10) Patent No.: US 9,279,660 B2
(45) Date of Patent: Mar. 8, 2016

(54) METHOD AND APPARATUS FOR PROCESSING POLARIZATION DATA OF POLARIZATION SENSITIVE OPTICAL COHERENCE TOMOGRAPHY

(71) Applicant: CANON KABUSHIKI KAISHA, Tokyo (JP)

(72) Inventors: Makoto Sato, Tokyo (JP); Mitsuro Sugita, Vienna (AU); Stefan Zotter, Vienna (AU); Michael Pircher, Vienna (AU); Christoph Hitzenberger, Vienna (AU)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/261,657

(22) Filed: Apr. 25, 2014

(65) Prior Publication Data

US 2014/0327917 A1    Nov. 6, 2014

(30) Foreign Application Priority Data

May 1, 2013   (JP) .................................. 2013-096531

(51) Int. Cl.
*G01B 9/02* (2006.01)
*A61B 3/10* (2006.01)
*G06T 5/50* (2006.01)

(52) U.S. Cl.
CPC ............ *G01B 9/02091* (2013.01); *A61B 3/102* (2013.01); *G01B 9/02087* (2013.01); *G06T 5/50* (2013.01); *G01B 2290/70* (2013.01); *G06T 2207/10101* (2013.01); *G06T 2207/20216* (2013.01); *G06T 2207/30041* (2013.01)

(58) Field of Classification Search
CPC ..... A61B 3/102; G01B 2290/70; G06F 17/18
See application file for complete search history.

(56) References Cited

U.S. PATENT DOCUMENTS

2010/0182609 A1*  7/2010  Wang et al. .................... 356/491
2011/0009752 A1*  1/2011  Chen et al. ..................... 600/478

FOREIGN PATENT DOCUMENTS

EP         2243420         10/2010

OTHER PUBLICATIONS

E. Goetzinger et al, "Speckle noise reduction in high speed polarization sensitive spectral domain optical coherence tomography", Optics Express, vol. 19(15), pp. 14568-14584 (Jul. 2011).
E. Goetzinger et al, "Polarization maintaining fiber based ultra-high resolution spectral domain polarization sensitive optical coherence tomography", Optics Express, vol. 17(25), pp. 22704-22717 (2009).
Park et al. "Real-time fiber-based multi-functional spectral-domain optical coherence tomography at 1.3 micrometers", Optics Express, XP551395986, May 2005, vol. 13, No. 11, pp. 3931-3944.
European Search Report issued in corresponding EP Application No. 14166792.3 on Sep. 4, 2014.
Zimlyakov D.A., "Optical Tomography of Tissues", Quantum Electronics No. 10 (32) 2002, pp. 854-867.
Russian Office Action issued in corresponding application No. 2014117464 on Oct. 7, 2015.

* cited by examiner

*Primary Examiner* — Michael A Lyons
*Assistant Examiner* — Shawn Decenzo
(74) *Attorney, Agent, or Firm* — Carter, DeLuca, Farrell & Schmidt, LLP

(57) ABSTRACT

A method for processing polarization data includes steps of acquiring a plurality of sets of polarization data items, converting the set of polarization data items into a representation including parameters of amplitude and phase, and averaging the converted set of polarization data items.

21 Claims, 12 Drawing Sheets

FIG. 9A
FIG. 9B
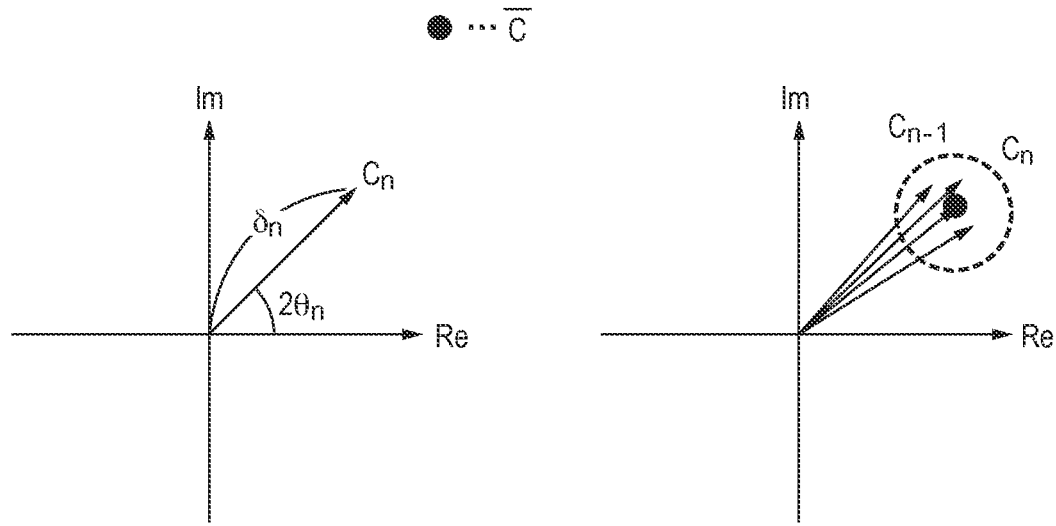
FIG. 9C
FIG. 9D
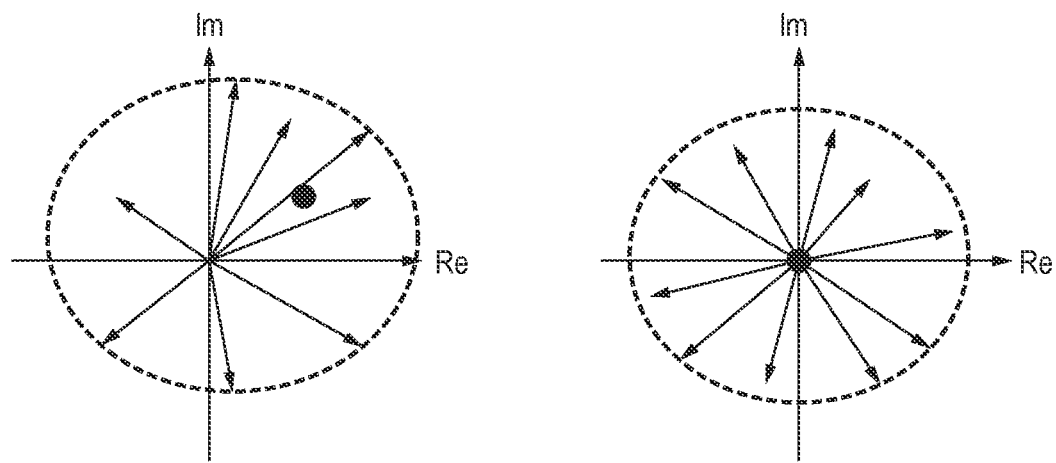

| Number of frames (N) | Present embodiment | Prior art |
|---|---|---|
| 1 | 2.58 | 8.61 |
| 5 | 1.54 | 5.08 |
| 10 | 0.8 | 3.96 |
| 20 | 1.3 | 3.33 |
| 30 | 1.25 | 3.07 |
| 50 | 1.18 | 2.73 |

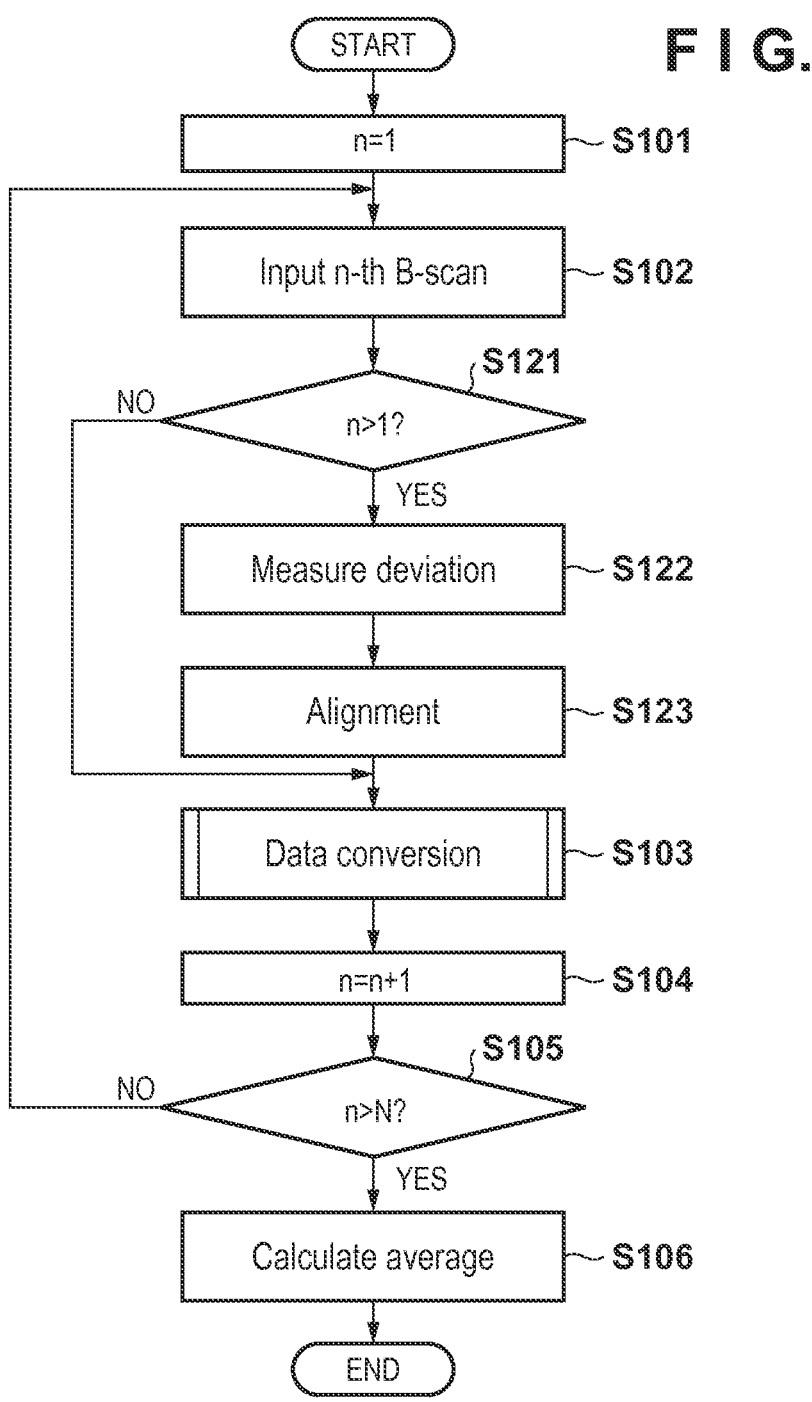

First B-scan n-th B-scan

METHOD AND APPARATUS FOR PROCESSING POLARIZATION DATA OF POLARIZATION SENSITIVE OPTICAL COHERENCE TOMOGRAPHY

BACKGROUND OF THE INVENTION

1. Field of the Invention

The present invention relates to method and apparatus for processing polarization data of polarization sensitive optical coherence tomography.

2. Description of the Related Art

Optical coherence tomography (hereinafter referred to as OCT) using multiple-wavelength optical interference can provide a high-resolution tomographic image of a sample (ocular fundus, in particular). In recent years, OCT apparatuses for ophthalmology have been studied to acquire a polarization sensitive OCT image for imaging the polarization parameter, which represents one of optical properties inherent to fundus tissues, in addition to an ordinary OCT image for imaging the shape of the fundus tissues.

By using polarization parameters, the polarization sensitive OCT apparatus can take a polarization sensitive OCT image and perform characteristic measurement or segmentation of the fundus tissues. The polarization sensitive OCT apparatus uses a beam that is modulated into a circularly-polarized beam as a measuring beam for observing a sample, and splits an interference beam into two linearly-polarized beams of orthogonal polarization states and detects the resulting two beams so as to generate polarization sensitive OCT images (see "E. Goetzinger et al, "Speckle noise reduction in high speed polarization sensitive spectral domain optical coherence tomography", Optics Express. 19(15), 14568-14584" (NPL 1)). Further, the polarization sensitive OCT is capable of imaging retardation as one of the polarization parameters, that is defined as phase difference between two polarized beam components. The retardation is useful to detect changes in a retinal nerve fiber layer for diagnosing glaucoma.

The literature further discloses a method of reducing the speckle noise peculiar to coherent light used for OCT by using plural polarization sensitive OCT images. According to the method, the speckle noise is reduced by averaging retardations that are obtained through the polarization sensitive OCT. As a result, the graininess of a resultant retardation image is significantly improved.

Retardation is defined as phase difference between a fast axis and a slow axis, which is observed when light passes through a medium. Therefore, it is useful to perform averaging considering angles which the fast axis and the slow axis form with the axis of the light used in an OCT apparatus (hereinafter referred to as an axis orientation). However, according to the method disclosed in NPL 1, the retardation is obtained on the basis of calculation of the arctangent of a ratio between the two polarized components (retardation=arctan (I1/I2)) and the retardation is obtained without referring to the axis orientation. Therefore, the value of the retardation necessarily falls within a range of 0 to 90°. This method uses only intensity of the two polarized components and noise has some intensity level that takes zero or positive value. For this reason, averaging of the noise does not converge to zero and introduces residual or offset. This offset in the case of low retardation value causes an undesirable artifact on an image. Thus, even in a case where a small signal is observed, when the retardation should approach 0, noise causes the retardation to have a non-zero value sometimes referred to as a retardation offset. In other words, by measuring retardation using intensities of the polarized components (as the conventional method does), noise in those intensities causes artifacts in the retardation value.

SUMMARY OF THE INVENTION

One embodiment of the present invention has been achieved to provide a method and a device for processing data, the method and the device reducing the occurrence of an artifact in retardation values through the use of plural polarization sensitive OCT images.

According to one aspect of the present invention, there is provided a method for processing polarization data of polarization-sensitive optical coherence tomography, comprising: an acquisition step of acquiring a plurality of sets of polarization data items obtained from light reflected from a sample to be measured; a conversion step of converting the polarization data items into a representation including parameters of amplitude and phase; and an averaging step of averaging the polarization data items that are expressed in the representation and generating a set of the averaged data items.

According to another aspect of the present invention there is provided an apparatus for processing polarization data of polarization-sensitive optical coherence tomography, comprising: an acquisition unit configured to acquire a plurality of sets of polarization data items obtained from a sample to be measured; a conversion unit configured to convert the polarization data items into a representation including parameters of amplitude and phase; and an averaging unit configured to average the polarization data items that are expressed in the representation and generating a set of the averaged data items.

Further features of the present invention will become apparent from the following description of exemplary embodiments with reference to the attached drawings.

BRIEF DESCRIPTION OF THE DRAWINGS

FIGS. 9A to 9D are diagrams illustrating processing expressed on a complex plane according to the embodiments of the present invention.

FIG. 12 illustrates a flowchart of data processing in the fourth embodiment, which includes alignment.

DESCRIPTION OF THE EMBODIMENTS

A data processing method according to the present invention can be applied to other samples without limiting the subject to organs or tissues including human eyes, and an imaging apparatus pertaining thereto includes but is not limited to an ophthalmic apparatus and an endoscope. Hereinafter, an ophthalmic apparatus will be described in detail with reference to drawings, as an exemplary apparatus of applying the present invention.

First Embodiment

Figure 1:
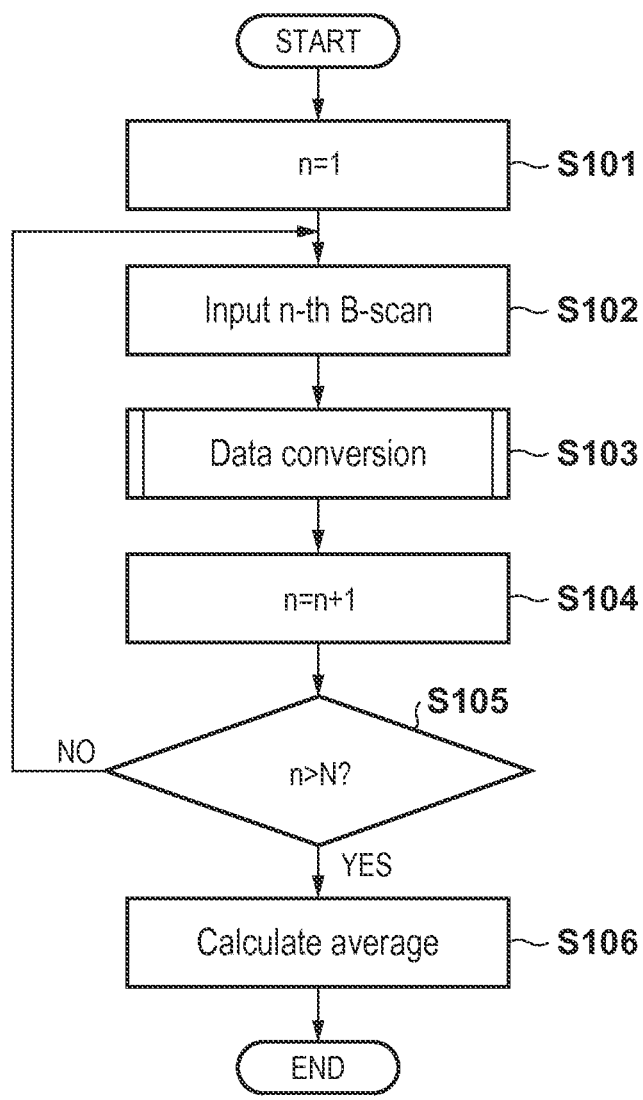
FIG. 1 is a flowchart illustrating a data processing method performed according to embodiments of the present invention.
Figure 2:
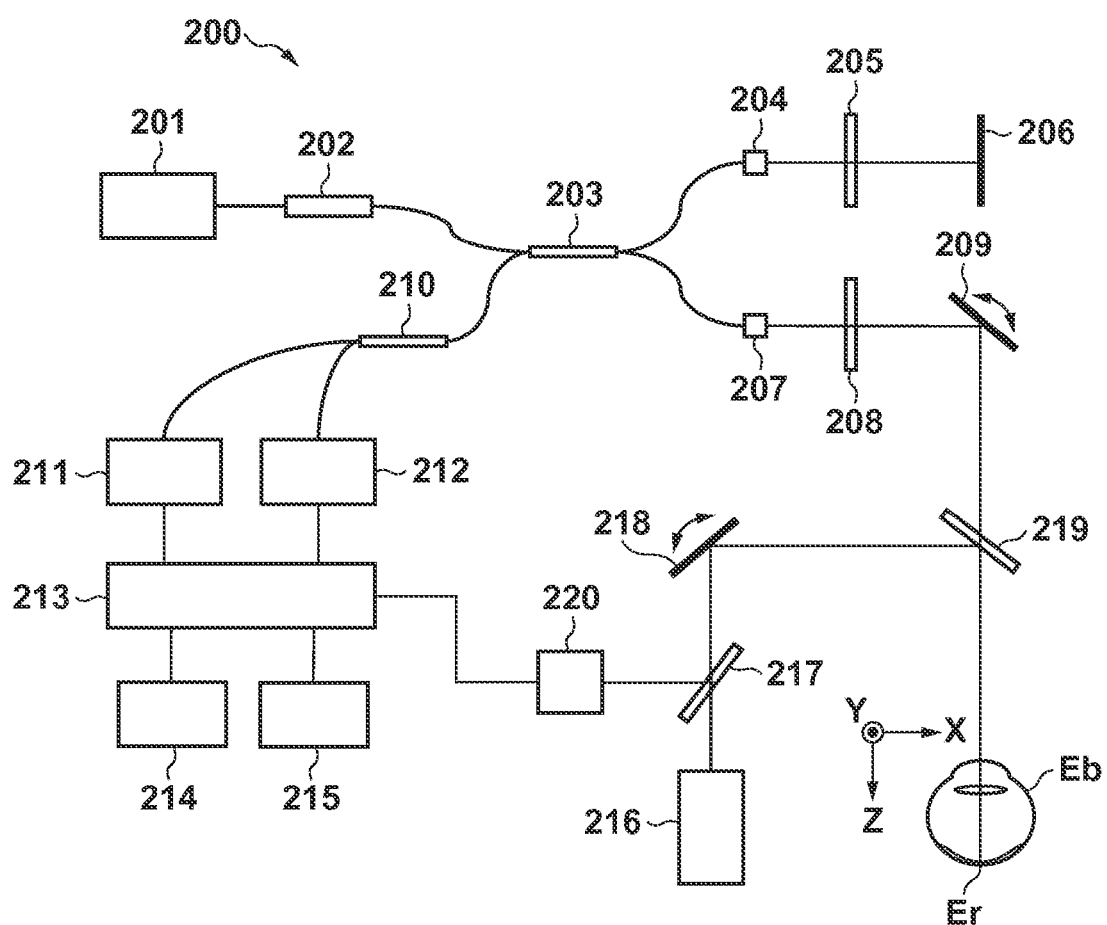
FIG. 2 illustrates the configuration of a polarization sensitive OCT imaging apparatus according to the embodiments of the present invention.

FIG. 1 is a flowchart of a polarization data processing method according to the present embodiment, FIG. 2 is a schematic view of a polarization sensitive OCT imaging apparatus 200 including a data processing device 213 according to the present embodiment. First, the configuration of the polarization sensitive OCT apparatus 200 will be described with reference to FIG. 2, and then the operations of the data processing device 213 according to the present embodiment will be described with reference to the flowchart of FIG. 1.

The polarization sensitive OCT apparatus 200 according to the embodiment includes a polarization sensitive OCT (Optical Coherence Tomography) system and a data processing device and constructs a polarization sensitive tomographic image by processing polarization data obtained from the polarization sensitive OCT system. In FIG. 2, measurement light emitted from a light source 201 is converted to linearly polarized light with a polarizer 202, and is input to a fiber coupler 203. The light source 201 is a super luminescent diode (SLD) light source that is a low-coherent light source, and emits light with a center wavelength of 850 nm and a band width of 50 nm, for example. Although the SLD is used as the light source 201, any light source capable of emitting low-coherent light such as an amplified spontaneous emission (ASE) light source may be used.

The fiber coupler 203 offers a 90:10 coupling ratio, for example, causes the measurement light to split at that ratio, and guides the split measurement light to a reference arm (splitting ratio of 90) including a collimator 204, a quarter wave plate 205, and a reference mirror 206, and a sample arm (splitting ratio of 10) including a collimator 207, a quarter wave plate 208, and a scanning mirror 209.

The measurement light guided to the reference arm passes through the quarter wave plate 205 installed in the state of being rotated 22.5 degrees. Upon being reflected by the reference mirror 206, the light becomes linearly polarized light via the quarter wave plate 205, and is again guided to the fiber coupler 203. On the other hand, the measurement light guided to the sample arm becomes circularly polarized light via the quarter wave plate 208 installed in the state of being rotated 45 degrees. The circularly polarized light is reflected by the scanning mirror 209, and is made incident on a subject's eye Eb that is a test sample to be measured.

Figure 3:
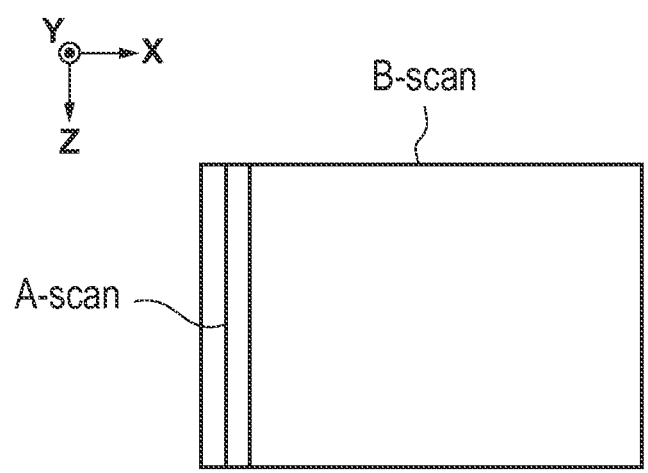
FIG. 3 illustrates a tomographic image.

Further, the measurement light is reflected by a retina Er, and is again guided to the fiber coupler 203 via the scanning mirror 209 and the quarter wave plate 208, and interferes with the measurement light that has passed through the reference arm. The scanning mirror 209 is controlled by a non-illustrated control device so as to deflect the measurement light in the X and Y directions, and the measurement result can be obtained as a scanned two-dimensional image of the retina. Additionally, in the following description, data acquired along a single line in beam direction is referred to as A-scan and data including at least two lengths of the A-scan arranged in the X-axis direction or the Y-axis direction is referred to as B-scan as illustrated in FIG. 3.

The interference light generated in the fiber coupler 203 is split into a horizontally polarized component light and a vertically polarized component light in the fiber coupler 210 including a polarized beam splitter, and the components are separately guided to the spectrometers 211 and 212 including a diffraction grating, a line camera, etc. Each of the guided interference light beams is separated into its spectral components, and the components are converted into electrical signals with the line camera and output to the data processing device 213 as spectrum data of horizontal polarization and vertical polarization.

The data processing device 213 functions as the polarization data processing apparatus according to the present embodiment, and may be realized using a personal computer (PC) or a digital circuit including an application specific integrated circuit (ASIC), etc. Further, 214 and 215 denote a display device including, for example, a liquid crystal monitor provided to display the data processing result and an input device provided to input an instruction from a user, which includes a keyboard, a mouse, etc.

From the above, the polarization sensitive OCT imaging apparatus 200 described in the present embodiment forms an OCT according to a spectral domain (SD) method. However, the present invention is not limited to the SD method. That is, the spirit of the present invention may also be applied, without being changed, to an imaging apparatus achieved according to at least a swept source (SS) method or a time domain (TD) method.

In the present embodiment, the data processing device 213 is realized by executing a data processing program stored in a memory connected to a non-illustrated PC by a central processing unit (CPU) installed in the PC. Further, control of operations of the entire polarization sensitive OCT imaging apparatus 200 is also performed by the CPU executing a device control program, and will be referred to as an imaging control device in the following description.

On the other hand, second measurement light with its center wavelength being different from that of the light source 201 is emitted from a semiconductor laser 216, and is made incident on the subject's eye Eb via a perforated mirror 217, a scanner mirror 218 capable of deflecting the second measurement light to the fundus in two axes including the X direction and the Y direction, and a dichroic mirror 219.

Figure 5:
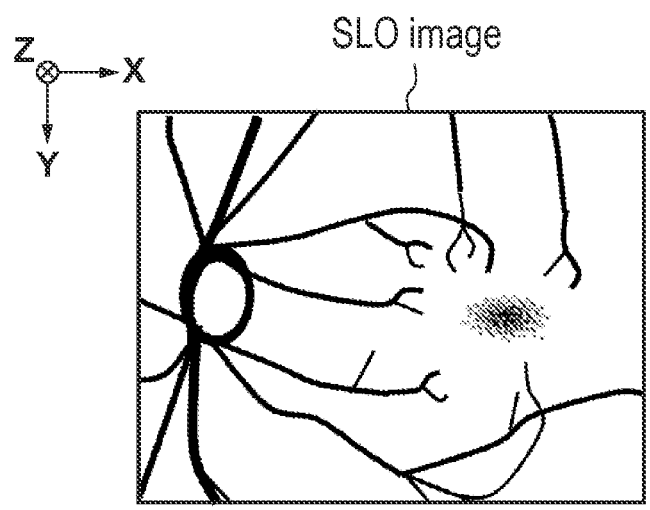
FIG. 5 illustrates an SLO image.

The second measurement light is also reflected by the retina Er, reflected by the dichroic mirror 219 and the scanner mirror 218 again, and is reflected by the perforated mirror 217 and made incident on a detector 220. The second measurement light, which is provided to obtain a planar image of the fundus through the two-dimensional scanning of measurement light, is input to the imaging control device so that the planar image is generated. FIG. 5 exemplarily illustrates the planar image referred to as an SLO (scanning laser ophthalmoscopy) image in the following description.

When acquiring the data of polarization sensitive OCT, the imaging control device acquires the SLO image in parallel therewith. Further, the imaging control device extracts data of a structure including blood vessels, etc. from the SLO image, detects the movements of the fundus, and controls the scanner mirror 209 so that measurement light of the polarization sensitive OCT can typically scan the same position on the retina.

Next, operations of the data processing device 213 will be described with reference to FIGS. 1 and 4.

Figure 4A:
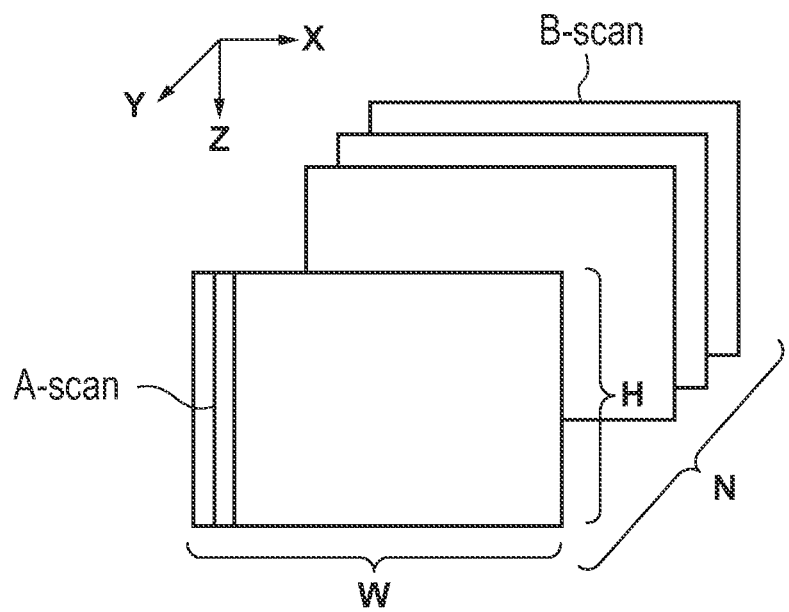
FIGS. 4A and 4B illustrate a tomographic image and a data acquisition position.
Figure 4B:
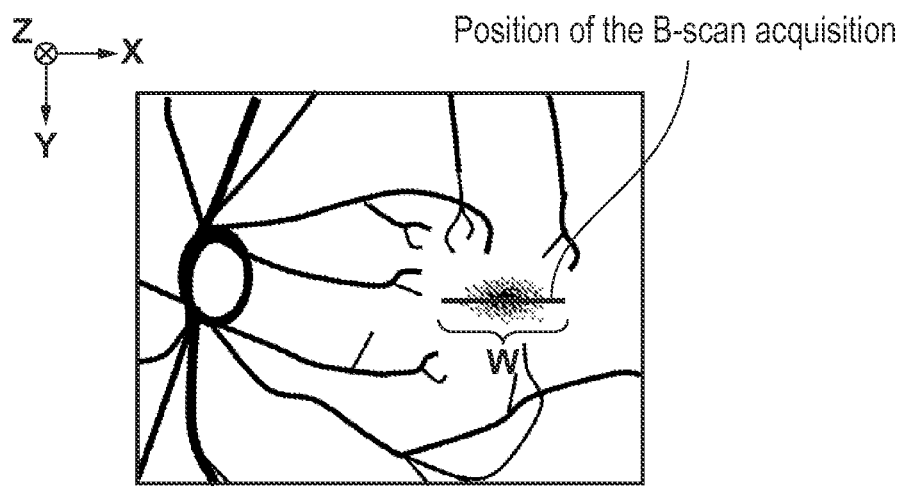

FIGS. 4A and 4B schematically illustrate data representing the sample structure which are generated by a process later described with the data acquired under control of the imaging control device according to the present embodiment. In the present embodiment, the B-scan including W lines of the A-scan (of depth H) is repeatedly acquired N times as illustrated in FIG. 4A. However, since no scanning is performed in the Y direction, N sheets of the B-scan are acquired, at different times, on the same position defined on the Y axis as shown in FIG. 4B. In FIGS. 4A and 4B, however, a single sheet of the B-scan includes the data of horizontal polarization and that in a vertical polarization.

First, the data processing device 213 initializes an internal counter n to 1 at step S101. As described later, the internal counter n, which increments the count by 1 every time the B-scan processing is performed, is provided so that the processing is repeatedly performed until the counter shows N.

Next, image data of the $n^{th}$ B-scan is input at step S102. As for the B-scan at that time, the imaging control device may acquire and store image data of N sheets of the B-scan in the memory in advance, or may repeatedly acquire data for each B-scan. Here, the $N^{th}$ sheet of the B-scan includes spectrum data $S_n^0$ of horizontal polarization and spectrum data $S_n^1$ of vertical polarization.

Figure 6:
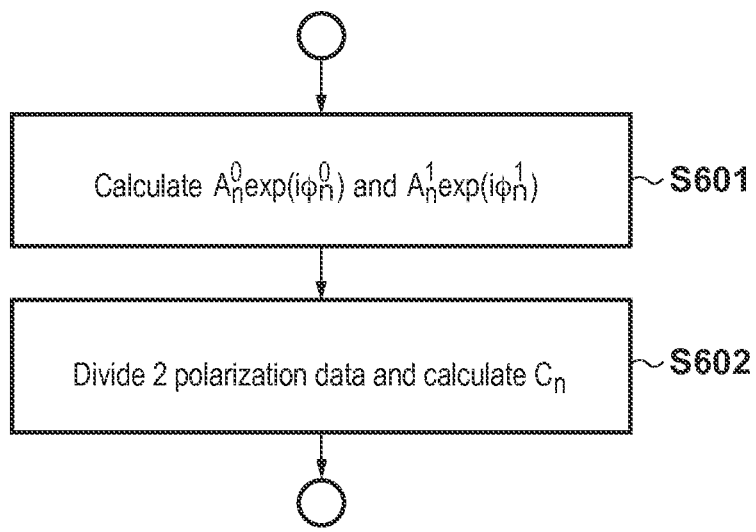
FIG. 6 is a part of flowchart illustrating data processing.

Next, conversion operations are performed for the input spectrum data items to achieve averaging at step S103. Processing performed at step S103 is described below with reference to FIG. 6.

At step S601, the data processing device 213 converts each of the above-described spectrum data items into tomography signals including parameters of amplitude and phase, which are shown as:

$$A_n^0 \exp(i\Phi_n^0)$$

$$A_n^1 \exp(i\Phi_n^1) \quad \text{(Expressions 1)}.$$

Here, $A_n^0$ and $A_n^1$ denote the amplitudes of the tomography signals, which are achieved by horizontal polarization and vertical polarization occurring for the n-th B-scan, respectively, and $\Phi_n^0$ and $\Phi_n^1$ denote the phases. That is, $$A_n^0 = \{A_0(x,z,n) | 1 \leq x \leq W, 1 \leq z \leq H, 1 \leq n \leq N\}$$

$$A_n^1 = \{A_1(x,z,n) | 1 \leq x \leq W, 1 \leq z \leq H, 1 \leq n \leq N\}$$

$$\Phi_n^0 = \{\Phi_0(x,z,n) | 1 \leq x \leq W, 1 \leq z \leq H, 1 \leq n \leq N\}$$

$$\Phi_n^1 = \{\Phi_1(x,z,n) | 1 \leq x \leq W, 1 \leq z \leq H, 1 \leq n \leq N\} \quad \text{(Expressions 2)}.$$

Here, W, H, and N are the number of the A-scan per the B-scan, the length of the A-scan and the number of the B-scan, respectively, as illustrated in FIGS. 4A and 4B. The above-described conversion is achieved by applying processing performed to convert the spectrum data into the tomography signals during OCT performed according to the SD method to the spectrum data $S_n^0$ of horizontal polarization and the spectrum data $S_n^1$ of vertical polarization. Since the conversion can be achieved according to the method disclosed in "E. Goetzinger et al, "Polarization maintaining fiber based ultra-high resolution spectral domain polarization sensitive optical coherence tomography", Optics Express. 17(25), 22704-22717 (2009)" (NPL 2), for example, the more detailed description is omitted.

Next, at step S602, the data processing device 213 divides the tomography signals relating to the two types of polarization shown in (Expression 1) by each other to calculate complex data $C_n$ including a retardation and an axis orientation that are obtained for the $n^{th}$ B-scan according to the following equation:

$$C_n = \tan^{-1}\left(\frac{A_n^1}{A_n^0}\right)\frac{\exp(i\Phi_n^1)}{\exp(i\Phi_n^0)} = \tan^{-1}\left(\frac{A_n^1}{A_n^0}\right)\exp(i(\Phi_n^1 - \Phi_n^0)). \quad \text{(Expression 3)}$$

On the other hand, a retardation $\delta_n$ and an axis orientation $\theta_n$ are defined by the following equations:

$$\delta_n = \tan^{-1}\left(\frac{A_n^1}{A_n^0}\right), \quad \text{(Expression 4)}$$

and $$\theta_n = \frac{(\pi - \Delta\phi_n)}{2}, \quad \text{(Expressions 5)}$$

where $$\Delta\phi_n = (\phi_n^1 - \phi_n^0).$$

Accordingly, $C_n$ becomes data including the retardation $\delta_n$ and the axis orientation $\theta_n$ as shown by the following equation:

$$C_n = \delta_n \exp(i(\pi - 2\theta_n)) \quad \text{(Expression 6)}.$$

As described above, the $C_n$ is obtained by dividing polarization data items relating to at least two different directions by each other as shown in (Expression 3). From Cn, two parameters can be extracted as shown in (Expression 4) and (Expression 5). These parameters are:

1. "phase retardation" is the phase difference between the beams whose electric field vector is oriented along the slow and the fast axis. This parameter is contained in the $C_n$ value of Expression 3 in the form of the arctan function and named δ in Expression 6.

2. The two complex signals as directly measured contain phase values $\Phi 0$ and $\Phi 1$, whose phase difference $\Delta\Phi = \Phi 1 - \Phi 0$ encodes the optic axis orientation θ. Therefore, there are actually two parameters that are contained in the result of the division: retardation $\delta_n$ and axis orientation $\theta_n$.

Then, $C_n$ becomes complex data which substantially includes retardation and axis orientation of the sample. That is, the complex data includes information relating to the retardation and axis orientation. The $C_n$ thus calculated is temporally stored in a non-illustrated memory provided in the data processing device 213.

Next, the processing returns again to the flowchart of FIG. 1 so that the current number of the B-scan is incremented by 1 at step S104, and it is determined whether or not the updated n is greater than the total B-scan number N at step S105.

When n does not exceed the total B-scan number N, the processing returns again to step S102 so that the above-stated processing is performed. When n exceeds the total B-scan number, the processing proceeds to step S106.

At step S106, the data processing device 213 calculates $\overline{C}$ obtained by averaging $C_n$ (n=1, . . . , N) that is calculated based on each B-scan.

$$\overline{C} = \frac{1}{N}\sum_{n=1}^{N} C_n = \frac{1}{N}\sum_{n=1}^{N} \delta_n \exp(i(\pi - 2\theta_n)) \quad \text{(Expression 7)}$$

Next, the data processing device 213 calculates averaged retardation $\overline{\delta}$ and axis orientation $\overline{\theta}$ according to the following equations:

$$\bar{\delta} = \text{abs}(\bar{C}) \quad \text{(Expressions 8)}$$

$$\bar{\theta} = -\frac{\arg(\bar{C})}{2} + \frac{\pi}{2}.$$

Here, retardation $\bar{\delta}$ and axis orientation $\bar{\theta}$ are expressed as follows, $$\bar{\delta} = \{\bar{\delta}(x,z) | 1 \leq x \leq W, 1 \leq z \leq H\}$$

$$\bar{\theta} = \{\bar{\theta}(x,z) | 1 \leq x \leq W, 1 \leq z \leq H\} \quad \text{(Expressions 9)}$$

and can be displayed as a retardation image and an axis orientation image on a plane constituted by the X axis and the Z axis as is the case with an ordinary tomographic image. That is, the value of a pixel provided at the position (x, z) may be $\bar{\delta}(x, z)$ for the retardation image, and may be $\bar{\theta}(x, z)$ for the axis orientation image.

The data processing device 213 generates images based on the retardation $\bar{\delta}$ and the axis orientation $\bar{\theta}$ that are calculated according to (Expressions 9), respectively, and outputs the generated images to the display device 214.

Figure 7:
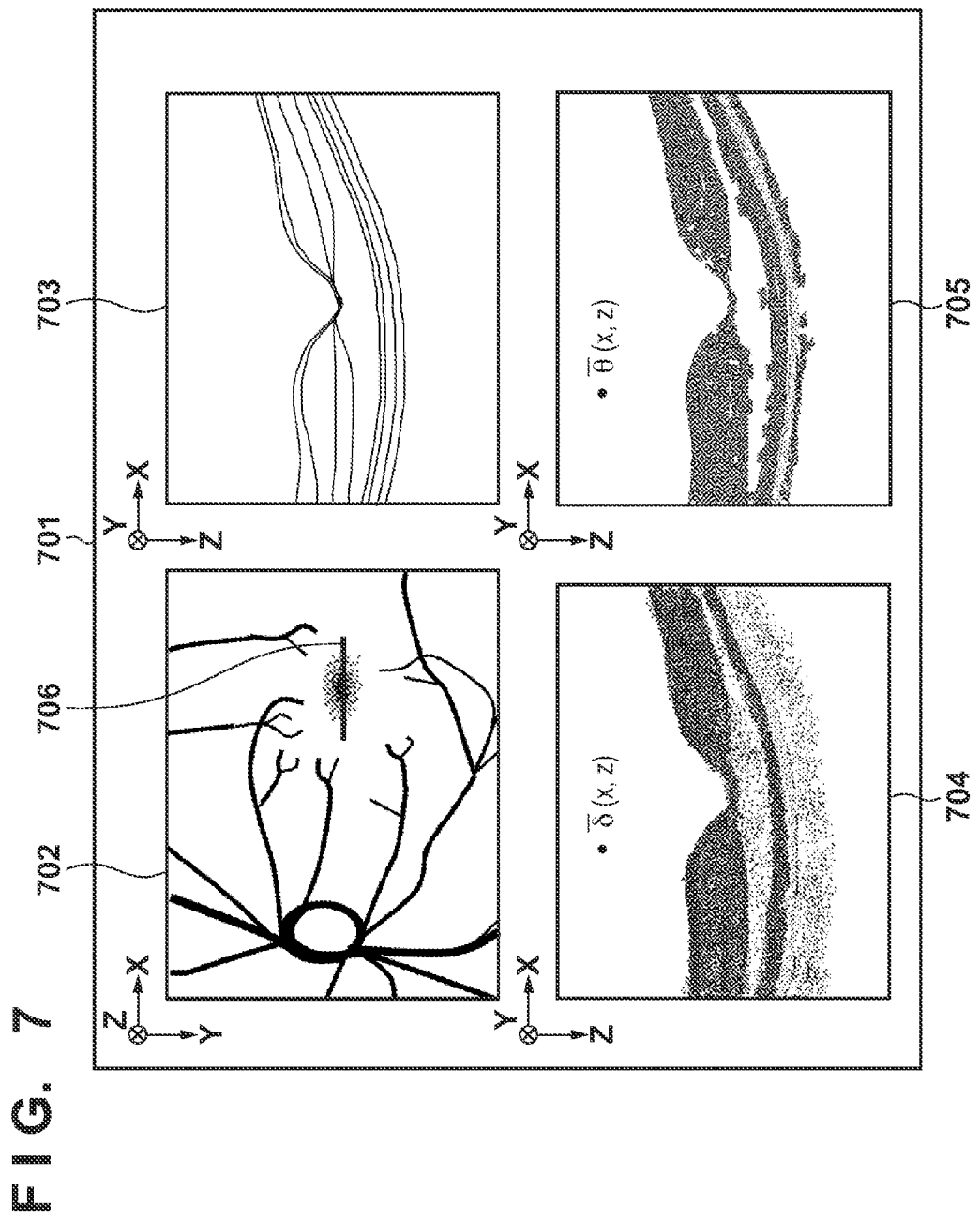
FIG. 7 illustrates exemplary images processed by using data.

FIG. 7 exemplarily illustrates a display mode used by the display device 214 according to the present embodiment. The display device 214 offers sub areas 702 to 705 in a display area 701. In the sub area 702, a cursor 706 is superimposed and displayed on the SLO image. The cursor 706 indicates the position where N units of the B-scan are acquired, and the averaged axis orientation $\bar{\theta}$ and retardation $\bar{\delta}$ are displayed in the sub areas 705 and 704.

Also, an intensity tomographic image at that position is displayed in the sub area 703. This intensity tomographic image may be obtained by, for example, calculating a value for each pixel using $\sqrt{(A_0(x, z, n)^2 + A_1(x, z, n)^2)}$ from amplitudes $A_n^0$ and $A_n^1$ of the tomography signals as shown in (Expression 2).

Figure 8:
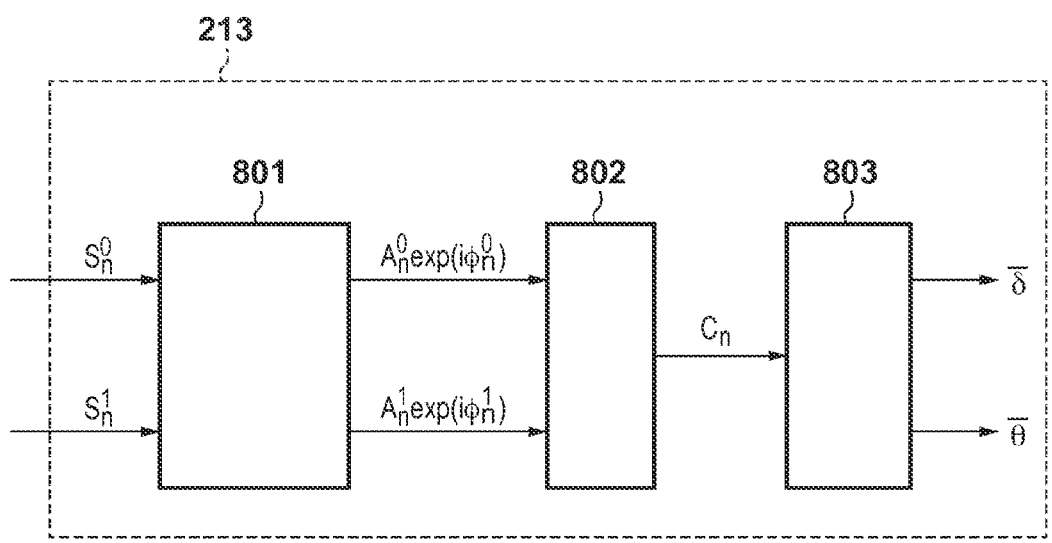
FIG. 8 illustrates data processing according to the embodiments of the present invention.

FIG. 8 shows the configuration of the above-described data processing device 213 and the data flow. In FIG. 8, a tomography signal-generation device 801 converts the spectrum data $S_n^0$ of horizontal polarization and the spectrum data $S_n^1$ of vertical polarization into the tomography signals $A_n^0 \exp(i\Phi_n^0)$, and $A_n^1 \exp(i\Phi_n^1)$, respectively, and outputs those tomography signals (step S601). Those tomography signals are divided by a divider 802, and the complex data $C_n$ shown in (Expressions 3) is output to an average calculator 803 (step S602). The average calculator 803 calculates and outputs the retardation $\bar{\delta}$ and the axis orientation $\bar{\theta}$ that are averaged based on (Expressions 7) and (Expressions 8) (step S106).

According to the above-described embodiment, the following advantages may be obtained.

The two tomography signals shown in (Expressions 1) are expressed as below:

$$A_n^0 \exp(i\Phi_n^0) = \sqrt{I_n} \cos(\delta_n) \exp(-i\delta_n) \exp(i\Phi_n^C)$$

$$A_n^1 \exp(i\Phi_n^1) = \sqrt{I_n} \sin(\delta_n) \exp(-i\delta_n + i(\pi - 2\theta_n)) \exp(i\Phi_n^C) \quad \text{(Expressions 10)}.$$

Here, $I_n$ denotes the reflectivity of the subject, and $\Phi_n^C$ denotes a phase term shared between both the polarized components that are obtained through the interference with the reference light. Here, the two tomography signals are divided by each other as shown by (Expressions 3) so that the reflectivity and phase of the subject, which are common terms, are cancelled so that a signal only including the retardation and the axis orientation is achieved as shown by (Expression 6).

FIG. 9A represents $C_n$ expressed by (Expression 6) on a complex plane, and the average value $\bar{C}$ calculated in the present embodiment is expressed as black dots shown in FIG. 9B to FIG. 9D. FIG. 9B expresses the state where a noise level is low. On the other hand, FIG. 9C expresses the state where the noise level is higher than in FIG. 9B, and FIG. 9D expresses the state where there is almost nothing but the noise. In that state, the value of the retardation becomes approximately zero, as a result of the averaging.

However, according to the known technology disclosed in NPL 1, the value of the retardation is calculated based on the amplitudes of the two polarized components as shown by the following expression, so that the retardation has a constant non-zero value under the condition expressed in FIG. 9D, which becomes an artifact and makes it difficult to represent a structure such as a Henle's fiber layer offering a minute retardation:

$$\bar{\delta}(x, z) = \frac{1}{N} \sum_{n=1}^{N} \tan^{-1}\left(\frac{A_1(x, z, n)}{A_0(x, z, n)}\right). \quad \text{(Expression 11)}$$

On the other hand, according to the present embodiment, the averaging is performed through the processing achieved with the representation of complex number including the amplitudes and the phases of the two polarized components. Therefore, the value of the minute retardation may be accurately calculated.

Figures 10A, 10B:
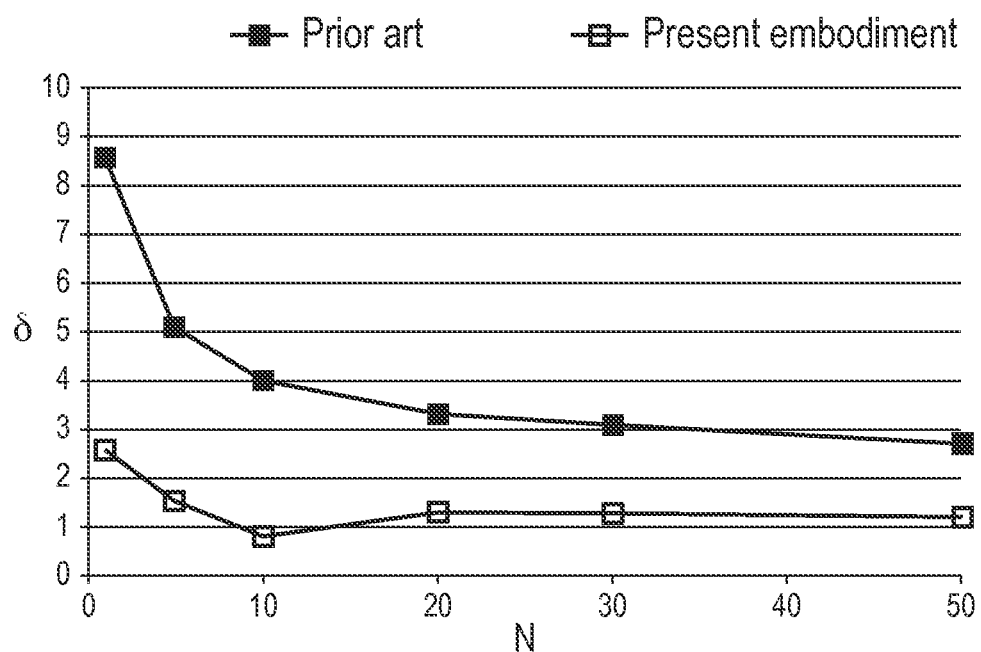
FIGS. 10A and 10B illustrate exemplary results of averaging processing according to the first embodiment.

Additionally, FIGS. 10A and 10B show an example that expresses the relationship between the number of averaged frames, which is expressed as N, and the average value of retardations, $\delta$. According to the drawing, the average value of the retardations is gradually reduced with increases in the number of averaged frames according to the known technology, while the average value becomes approximately constant for numbers N larger than 10 according to the method of the present embodiment, which indicates that the averaging is appropriately performed.

Additionally, the complex data $C_n$ may be calculated according to the following expression without being limited to (Expression 3):

$$C_n = \frac{A_n^1 \exp(i\Phi_n^1)}{A_n^0 \exp(i\Phi_n^0)} = \tan(\delta_n)\exp(i(\Phi_n^1 - \Phi_n^0)). \quad \text{(Expression 12)}$$

In that case, $\bar{C}$, and the averaged retardation $\bar{\delta}$ and axis orientation $\bar{\theta}$ are expressed as:

$$\bar{C} = \frac{1}{N}\sum_{n=1}^{N} C_n = \frac{1}{N}\sum_{n=1}^{N}\tan(\delta_n)\exp(i(\pi - 2\theta_n)) \quad \text{(Expressions 13)}$$

$$\bar{\delta} = \tan^{-1}(\text{abs}(\bar{C}))$$

$$\bar{\theta} = -\frac{\arg(\bar{C})}{2} + \frac{\pi}{2}.$$

Second Embodiment

In the above-described first embodiment, the average value is calculated by dividing the two tomography signals, but averaging of each of the signals is also possible.

That is, averaging is performed for each of the tomography signals expressed by (Expressions 1) to calculate the retardation and the axis orientation. In that case, the data processing device 213 calculates the averaged tomography signals according to the equations:

$$\overline{A_0} = \frac{1}{N}\sum_{n=1}^{N} A_n^0 \exp(i\Phi_n^0)$$

$$\overline{A_1} = \frac{1}{N}\sum_{n=1}^{N} A_n^1 \exp(i\Phi_n^1)$$

$$\overline{\delta} = \tan^{-1}\left(\frac{\mathrm{abs}(\overline{A_1})}{\mathrm{abs}(\overline{A_0})}\right)$$

$$\overline{\theta} = \frac{(180° - (\arg(\overline{A_1}) - \arg(\overline{A_0})))}{2}.$$

(Expressions 14)

Additionally, when the averages are calculated according to (Expressions 14) and the number N is high, there is a possibility that the signal component is cancelled and the SNR is reduced, because the phases $\Phi_n^0$ and $\Phi_n^1$ may be independently fluctuated by phase jitter for each measurement. Accordingly, when elapsed time for data acquisition exceeds certain amount, it is preferable that the averaging be performed according to the method described in the first embodiment.

On the other hand, the division must be performed for every piece of data according to the first embodiment. However, since the division is not performed before calculating the average in the present embodiment, the calculation load becomes relatively low, which is beneficial. Therefore, depending on the value of N, the average calculation may be performed at a higher speed by selecting the method of the present embodiment.

Alternatively, modified (Expression 14) can be used for calculating averaged tomography signals. In this case, the phase of one tomography signal is ignored while other phase is maintained. For example, the phase term $\exp(i\Phi_n^0)$ is set to 1 and $\exp(i\Phi_n^1)$ is changed to $\exp(i(\Phi_n^1 - \Phi_n^0))$ in (Expression 14). By this modification, cancelling the signal component and SNR (signal-to-noise ratio) reduction are avoided. This modification is effective for the case of moving subject or non-negligible seismic noises during the measurement.

Third Embodiment

According to the first embodiment stated above, data are acquired over N times by taking scans of the same position defined on the retina as shown in FIG. 4B, and the averaging is performed for the N pieces of data existing at the same place in terms of space. However, the present invention may be achieved without being limited thereto. In a manner to be described, the set of polarization data items includes polarization data items acquired in different spatial positions.

Figure 11A:
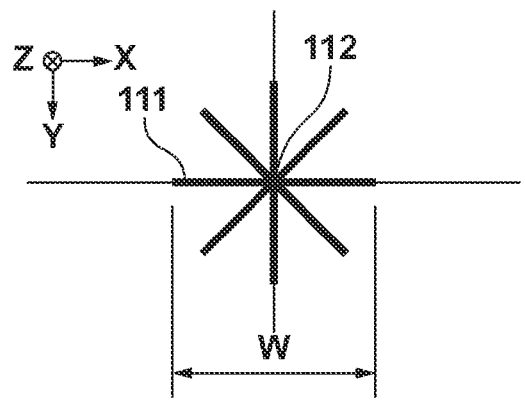
FIGS. 11A to 11C illustrate other examples of data acquisition.

FIG. 11A illustrates an example. In FIG. 11A, pieces of the B-scan are arranged in a radial manner as indicated by 111, using an optic nerve head 112 as a center, and N sheets of the B-scan are acquired in four directions in all. In this example, the averaging is performed according to the method described in the first embodiment in each direction.

Figure 11B:
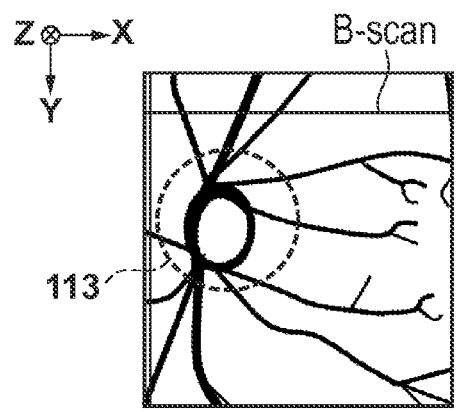
Figure 11C:
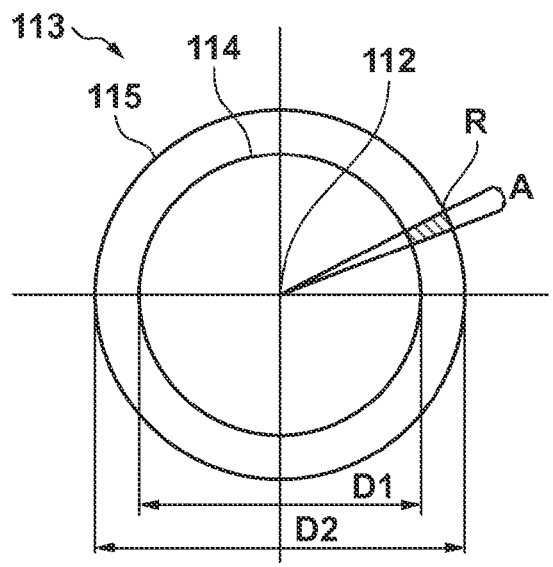

Additionally, an example where the averaging is performed for a spatial region is shown in FIGS. 11B and 11C. In the present embodiment, the polarization sensitive OCT imaging apparatus 200 acquires pieces of the B-scan while shifting in the Y direction as shown in FIG. 11B, and the data processing device 213 performs data processing for a measurement region 113 including the optic nerve head according to the method described below.

FIG. 11C illustrates the details of the measurement region 113. In this drawing, a region R that is split off at a predetermined angle A from two concentric circles 114 and 115 of diameters D1 and D2, having the optic nerve head 112 as their center, is determined to be the target region for averaging. Although D1 and D2 are 2 mm and 3 mm, for example, and A is 1° in the present embodiment, those values may be determined in accordance with precision required to measure the retinal nerve fiber layer.

In that case, the averaging is performed for A-scans belonging to the region R, and targeted tomography signals are expressed as follows:

$$A_r^0 = \{A_0(r,z) | r = (x,y), r \in R, 1 \le z \le H\}$$

$$A_r^1 = \{A_1(r,z) | r = (x,y), r \in R, 1 \le z \le H\}$$

$$\Phi_r^0 = \{\Phi_0(r,z) | r = (x,y), r \in R, 1 \le z \le H\}$$

$$\Phi_r^1 = \{\Phi_1(r,z) | r = (x,y), r \in R, 1 \le z \le H\}$$

(Expressions 15).

Complex data $C_r$ averaged in the present embodiment is expressed as:

$$C_r = \delta_r \exp(i(\pi - 2\theta_r))$$

(Expression 16), and the data processing device 213 calculates a retardation $\overline{\delta}$ and an axis orientation $\overline{\theta}$ that are averaged for the region R, while determining the number of pieces of the A-scan included in the region R to be M, according to the equation:

$$\overline{C} = \frac{1}{M}\sum_{r \in R} C_r = \frac{1}{M}\sum_{r \in R} \delta_r \exp(i(\pi - 2\theta_r)).$$

(Expression 17)

Next, the data processing device 213 calculates the averaged retardation $\overline{\delta}$ and axis orientation $\overline{\theta}$ according to the following equations as is the case with (Expressions 8):

$$\overline{\delta} = \mathrm{abs}(\overline{C})$$

$$\overline{\theta} = -\frac{\arg(\overline{C})}{2} + \frac{\pi}{2}.$$

(Expressions 18)

Here, equations of the averaged retardation $\overline{\delta}$ and axis orientation $\overline{\theta}$ are expressed as follows:

$$\overline{\delta} = \{\overline{\delta}(r,z) | r = (x,y), r \in R, 1 \le z \le H\}$$

$$\overline{\theta} = \{\overline{\theta}(r,z) | r = (x,y), r \in R, 1 \le z \le H\}$$

(Expressions 19)

The above-described processing is successively performed by moving the position of R along an area surrounded by the concentric circles 114 and 115, and the average values are calculated at each position, so that the distributions of retardations and axis orientations occurring around the optic nerve head may be measured.

Fourth Embodiment

Present invention can be applied to interpolation for data of polarization sensitive OCT. In this embodiment, application of the present invention for data alignment used for averaging of plural B-scans, aforementioned in the first embodiment, is described.

Figure 13A:
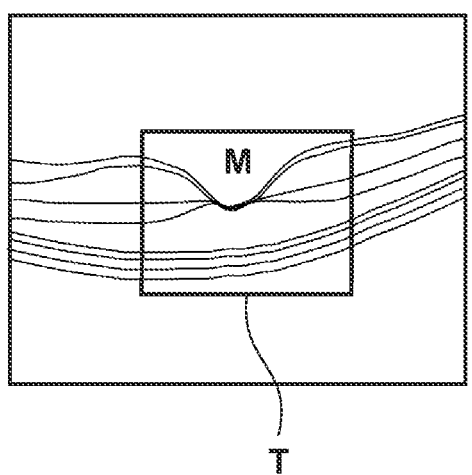
FIGS. 13A and 13B illustrate alignment for B-scans.
Figure 13B:
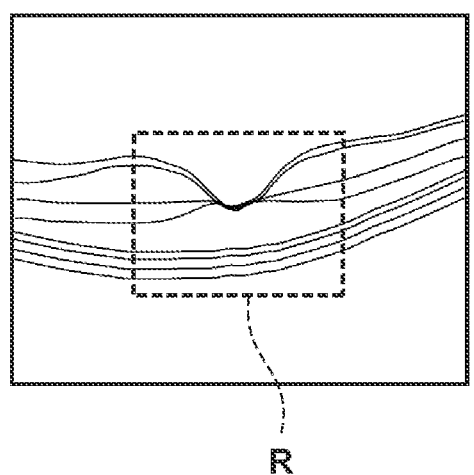

FIG. 12 is a flowchart of a data processing method according to the present embodiment. Because it is a modification of the flowchart shown in FIG. 1 by adding step S121, S122 and S123, duplicate descriptions are omitted. Also, FIGS. 13A and 13B shows the template region T for template matching in first B-scan and $n^{th}$ B-scan.

At step S121, the data processing device 213 identifies whether immediately previous B-scan ($n^{th}$ B-scan) is first scan or not. In the case of the first B-scan, the process goes to step S103, otherwise step S122.

At step S122, measurement of the relative deviation between the previous B-scan ($n^{th}$ B-scan) and the first B-scan is performed by the data processing device 213. Firstly, a template region T is determined using the first B-scan as shown in FIGS. 13A and 13B. It is preferable to define the template region T for template matching so that it includes geometric features in the B-scan such like fovea centralis M as shown in FIGS. 13A and 13B.

In the present embodiment, template matching is applied to an intensity tomographic image $I_n$ which is calculated with two polarization components of the tomogram signals, $A_0(x,z,n)$ and $A_1(x,z,n)$ as shown by following equation:

$$I_n = \{I(x,z,n) | 1 \le x \le W, 1 \le z \le H, 1 \le n \le N\}$$

$$I(x,z,n) = \sqrt{A_0(x,z,n)^2 + A_1(x,z,n)^2} \quad \text{(Expression 20)}.$$

Next, the template matching is applied by the data processing device 213 and a region R which is most correlated to the template region T in $n^{th}$ B-scan $I_n$, and relative deviations between T and R are detected as $\Delta X$ and $\Delta Y$.

At the step S123, alignment of $n^{th}$ B-scan $I_n$ using $\Delta X$ and $\Delta Y$ is taken place by the data processing device 213 so that same subject is aligned at same position in the two B-scans. Generally, because $\Delta X$ and $\Delta Y$ are not integer numbers, interpolation is necessary for the data of $n^{th}$ B-scan.

In the following description, bi-linear is utilized as interpolation method, however present invention can be applied to other method such as bi-cubic interpolation by changing the data range and weighting coefficients.

The data processing device 213 calculates each coordinate value x and z of the B-scan data after the alignment using $\Delta X$ and $\Delta Y$, then a complex data $\hat{C}_n$ is calculated which is a modified complex data of $C_n$ after the coordinate conversion as shown by the following equations.

$$\hat{C}(x2, z2, n) = [w_1 \quad w_2] \begin{bmatrix} C(x, z, n) & C(x+1, z, n) \\ C(x, z+1, n) & C(x+1, z+1, n) \end{bmatrix} \begin{bmatrix} w_3 \\ w_4 \end{bmatrix} \quad \text{(Expression 21)}$$

$$C(x, z, n) = \tan^{-1}\left(\frac{A_1(x, z, n)}{A_0(x, z, n)}\right)$$

$$\exp(i(\Phi_1(x, z, n) - \Phi_0(x, z, n))).$$

Where in $w_1$ to $w_4$ are weighting coefficients of bi-linear interpolation calculated as follows.

$$w_1 = \lfloor x \rfloor + 1 - x$$

$$w_2 = x - \lfloor x \rfloor$$

$$w_3 = \lfloor z \rfloor + 1 - z$$

$$w_4 = z - \lfloor z \rfloor \quad \text{(Expression 22)}.$$

$\hat{C}(x2, z2, n)$ corresponds to the complex data at position (x2, z2) in the $n^{th}$ B-scan after position correction (the alignment). Next, the calculated complex data are averaged by (Expression 23) and averaged retardation $\bar{\delta}$ and axis orientation $\bar{\theta}$ are calculated according to (Expression 8) as described in the first embodiment.

$$\bar{C} = \frac{1}{N} \sum_{n=1}^{N} \hat{C}_n. \quad \text{(Expression 23)}$$

In this embodiment, the complex data of (Expression 21) is calculated according to the first embodiment. However any calculation for generating the complex data such as that in the second embodiment is applicable.

Fifth Embodiment

The aforementioned embodiments utilize Jones vector for representing polarization data items. However, the present invention is not limited to this and the Stokes vector representation can be applied.

Because basic processing flow is the same as FIG. 1 applied to the other embodiments, only different steps are described in the following description.

Figure 14:
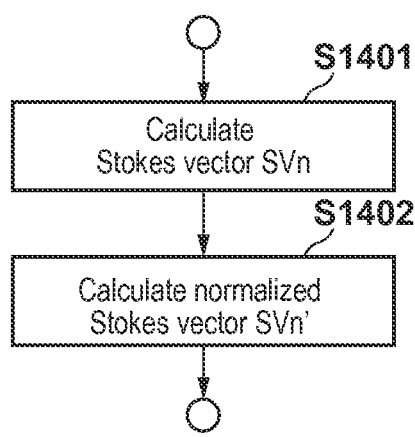
FIG. 14 illustrates a flowchart of a data conversion step according to the present embodiment.

FIG. 14 is a flowchart of a data conversion step S103 according to the present embodiment.

At step 1401, the data processing device 213 calculates the Stokes vector $SV_n$ as the $n^{th}$ polarization data item to be averaged. The Stokes vector $SV_n$ is calculated by (Expression 24).

$$SV_n = \begin{bmatrix} I_n \\ Q_n \\ U_n \\ V_n \end{bmatrix} \quad \text{(Expression 24)}$$

$$I_n = \{A_0(x, z, n)^2 + A_1(x, z, n)^2 \mid 1 \le x \le W,$$
$$1 \le z \le H, 1 \le n \le N\}$$

$$Q_n = \{A_0(x, z, n)^2 - A_1(x, z, n)^2 \mid 1 \le x \le W,$$
$$1 \le z \le H, 1 \le n \le N\}$$

$$U_n = \{2A_0(x, z, n)A_1(x, z, n)\cos(\Delta\Phi(x, z, n)) \mid 1 \le x \le W,$$
$$1 \le z \le H, 1 \le n \le N\}$$

$$V_n = \{2A_0(x, z, n)A_1(x, z, n)\sin(\Delta\Phi(x, z, n)) \mid 1 \le x \le W,$$
$$1 \le z \le H, 1 \le n \le N\}$$

Where $$\Delta\Phi(x, z, n) = \Phi_1(x, z, n) - \Phi_0(x, z, n).$$

At the next step S1402, the data processing device 213 calculates a normalized Stokes vector $SV_n'$ according to (Expression 25).

$$SV_n' = \begin{bmatrix} Q_n/I_n \\ U_n/I_n \\ V_n/I_n \end{bmatrix} = \begin{bmatrix} Q_n' \\ U_n' \\ V_n' \end{bmatrix}. \quad \text{(Expression 25)}$$

Figure 15:
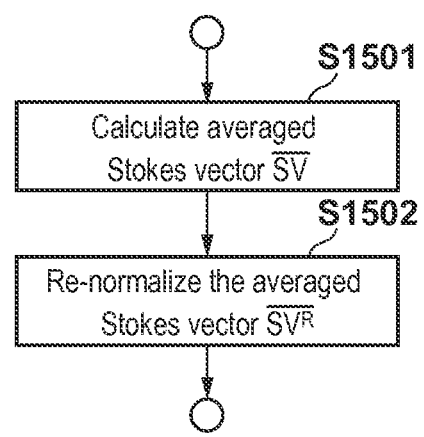
FIG. 15 illustrates a flowchart of a process for calculating averaged Stokes vector.

At the step S106, the data processing device 213 calculates an averaged Stokes vector according to the flowchart in FIG. 15. At step S1501, the data processing device 213 calculates an intermediate averaged Stokes vector $\overline{SV}^{int}$ according to (Expression 26).

$$\overline{SV}^{int} = \frac{1}{N} \begin{bmatrix} \sum_{n=1}^{N} Q'_n \\ \sum_{n=1}^{N} U'_n \\ \sum_{n=1}^{N} V'_n \end{bmatrix} = \begin{bmatrix} \overline{Q}^{int} \\ \overline{U}^{int} \\ \overline{V}^{int} \end{bmatrix} \quad \text{(Expression 26)}$$

Where $\overline{Q}^{int} = \{\overline{Q}^{int}(x,z) \mid 1 \le x \le W, 1 \le z \le H\}$ $\overline{U}^{int} = \{\overline{U}^{int}(x,z) \mid 1 \le x \le W, 1 \le z \le H\}$ $\overline{V}^{int} = \{\overline{V}^{int}(x,z) \mid 1 \le x \le W, 1 \le z \le H\}.$ Next, the data processing device 213 applies normalization again to the intermediate averaged Stokes vector $\overline{SV}^{int}$ and outputs the averaged Stokes vector $\overline{SV} = \{\overline{SV}(x,z) \mid 1 \le x \le W, 1 \le z \le H\}$ according to (Expression 27).

$$\overline{SV}(x \cdot z) = \begin{bmatrix} \overline{Q}^{int}(x \cdot z) / \sqrt{\overline{Q}^{int}(x,z)^2 + \overline{U}^{int}(x,z)^2 + \overline{V}^{int}(x,z)^2} \\ \overline{U}^{int}(x \cdot z) / \sqrt{\overline{Q}^{int}(x,z)^2 + \overline{U}^{int}(x,z)^2 + \overline{V}^{int}(x,z)^2} \\ \overline{V}^{int}(x \cdot z) / \sqrt{\overline{Q}^{int}(x,z)^2 + \overline{U}^{int}(x,z)^2 + \overline{V}^{int}(x,z)^2} \end{bmatrix} = \begin{bmatrix} \overline{Q}(x,z) \\ \overline{U}(x,z) \\ \overline{V}(x,z) \end{bmatrix}. \quad \text{(Expression 27)}$$

The averaged retardation $\overline{\delta}$ is calculated with two averaged amplitudes $\overline{A_0}$ and $\overline{A_1}$ according to (Expression 14). Also, those amplitudes can be calculated from Stokes parameter according to (Expression 24). Because of the two normalization processes according to (Expression 25) and (Expression 27), the averaged Stokes vector $\overline{SV}$ is normalized in regard to the intensity of the polarization data which is equal to 1.

Therefore, the data processing device 213 calculates the averaged retardation $\overline{\delta}$ according to the following expression.

$$\overline{\delta}(x,z) = \tan^{-1}\left(\sqrt{\frac{1 - \overline{Q}(x,z)}{1 + \overline{Q}(x,z)}}\right). \quad \text{(Expression 28)}$$

In a similar way, the averaged axis orientation $\overline{\theta}$ can be calculated based on (Expression 24) using the averaged Stokes vector parameters as follows.

$$\overline{\theta}(x,z) = \frac{\pi - \overline{\Delta\Phi}(x,z)}{2} \quad \text{(Expression 29)}$$

where $$\overline{\Delta\Phi}(x,z) = \tan^{-1}\left(\frac{\overline{V}(x,z)}{\overline{U}(x,z)}\right).$$

In the present embodiment, the averaging is performed on the Stokes vector which represents polarization status of light backscattered by the sample. Just after the averaging is made according to (Expression 26), the resultant vector does not necessarily maintain the relation among each parameter as given with (Expression 24), which introduces unwanted offset on calculating the retardation according to (Expression 28). However, because of the normalization by (Expression 27), the relation is recovered hence introducing such offset is avoided.

Sixth Embodiment

Although normalization before the averaging process is desirable, other implementation is also possible in present invention. In this embodiment, weighting average by intensity of the polarization data is applied.

In this embodiment, the data processing device 213 skips step 1402. Therefore the intermediate averaged Stokes vector $\overline{SV}^{int}$ is calculated according to (Expression 30) and followed by same steps as described in the fifth embodiment.

$$\overline{SV}^{int} = \frac{1}{N} \begin{bmatrix} \sum_{n=1}^{N} Q_n \\ \sum_{n=1}^{N} U_n \\ \sum_{n=1}^{N} V_n \end{bmatrix} = \begin{bmatrix} \overline{Q}^{int} \\ \overline{U}^{int} \\ \overline{V}^{int} \end{bmatrix}. \quad \text{(Expression 30)}$$

Differently from the fifth embodiment, each Stokes parameter is not normalized in regard to the intensity of the polarization data. In other words, the Stokes parameters in (Expression 30) depend on the intensity of the polarization data hence conceptually weighted.

However, step S1502, which is the second normalization process, recovers the relation among the Stokes parameters as described. Therefore the averaged retardation and axis orientation can be calculated correctly.

Because the first element of the Stokes vector in (Expression 24) is not necessary to calculate and the normalization before averaging is not performed, the computational efficiency is improved in this embodiment.

Seventh Embodiments

By being combined with the method disclosed in NPL 1, the present invention may also be effectively performed. That is, when less noise is generated and the variability of the complex data $C_n$ is insignificant as illustrated in FIG. 9B, the errors of retardation and axis orientation are small when they are calculated according to a known method. Therefore, the intensity of a signal is calculated in the first place based on the tomographic image signal shown in (Expressions 1). When the signal intensity exceeds a threshold value, average values may be calculated according to the method disclosed in NPL 1, which are expressed by the following equations. Otherwise, the method may be changed to that achieved by the present invention.

$$\overline{\delta} = \frac{1}{N} \sum_n \tan^{-1}\left(\frac{A_n^1}{A_n^0}\right) \quad \text{(Expression 31)}$$

$$\overline{\theta} = \frac{(180° - \text{MODE}(\Phi_n^1 - \Phi_n^0))}{2}.$$

However, MODE(X) is a mode value of the histogram of X, and the intensity of the tomography signal may be calculated based on the root mean square of its amplitude value. Further, the threshold value may be set based on the average of an intensity distribution of a retinal nerve fiber layer of a healthy subject, the intensity distribution being analyzed in advance.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-096531, filed May 1, 2013, which is hereby incorporated by reference herein in its entirety.

What is claimed is:

1. A method for processing polarization data of polarization-sensitive optical coherence tomography, comprising:
   detecting light, the light being obtained by splitting combined light using a polarization beam splitter, the combined light being obtained by combining return light from a sample to be measured irradiated with measuring light and reference light corresponding to the measuring light;
   acquiring a plurality of sets of polarization data items obtained from the detected light;
   converting the plurality of sets of the polarization data items into a representation in vector form including information regarding retardation and axis orientation;
   averaging the plurality of sets of the converted polarization data items that are expressed in the representation;
   calculating retardation and axis orientation from the plurality of sets of the averaged polarization data items;
   generating polarization-sensitive B-scan images of different types by using the calculated retardation and axis orientation; and
   causing a display unit to display at least one of the generated polarization-sensitive B-scan images.

2. The method for processing polarization data according to claim 1, wherein the plurality of sets of the polarization data items are converted into the representation by dividing polarization data items relating to at least two different directions by each other, and converting a phase difference between two polarization data items into the axis orientation included in the representation.

3. The method for processing polarization data according to claim 1, wherein the plurality of sets of the polarization data items are converted into the representation by dividing polarization data items relating to at least two different directions by each other, and generating complex data which includes retardation and axis orientation of the sample.

4. The method for processing polarization data according to claim 1, wherein the set of polarization data items includes polarization data items acquired at different times.

5. The method for processing polarization data according to claim 1, wherein the set of polarization data items includes polarization data items acquired in different spatial positions.

6. The method for processing polarization data according to claim 1, wherein the plurality of sets of the polarization data items are converted into the representation by calculating sets of Stokes vectors as the sets of polarization data items.

7. The method for processing polarization data according to claim 1, wherein the plurality of sets of the converted polarization data items that are expressed in the representation are averaged by generating averaged Stokes vectors as averaged polarization data items and normalizing the averaged Stokes vectors to give a norm of 1 in regard to the intensity of the polarization data items.

8. The method for processing polarization data according to claim 1, wherein the plurality of sets of polarization data items are obtained by a polarization-sensitive optical coherence tomographic apparatus imaging the sample, the polarization-sensitive optical coherence tomographic apparatus being communicably connectable.

9. The method for processing polarization data according to claim 1,
   wherein a retardation image and an axis orientation image are generated, as the polarization-sensitive B-scan images, by using the calculated retardation and axis orientation.

10. The method for processing polarization data according to claim 1, wherein the sample is an eye.

11. An apparatus for processing polarization data of polarization-sensitive optical coherence tomography, comprising:
    a detector configured to detect light, the light being obtained by splitting combined light using a polarization beam splitter, the combined light being obtained by combining return light from a sample to be measured irradiated with measuring light and reference light corresponding to the measuring light;
    an acquisition unit configured to acquire a plurality of sets of polarization data items obtained from the detected light;
    a conversion unit configured to convert the plurality of sets of the polarization data items into a representation in vector form including information regarding retardation and axis orientation;
    an averaging unit configured to average the plurality of sets of the converted polarization data items that are expressed in the representation;
    a calculating unit configured to calculate retardation and axis orientation from the plurality of sets of the averaged polarization data items;
    a generating unit configured to generate polarization-sensitive B-scan images of different types by using the calculated retardation and axis orientation; and
    a control unit configured to cause a display unit to display at least one of the generated polarization-sensitive B-scan images, wherein the acquisition unit, the conversion unit, the averaging unit, the calculating unit, the generating unit, and the control unit are implemented by at least one processor.

12. The apparatus for processing polarization data according to claim 11, wherein the conversion unit is operable to execute a calculation for dividing polarization data items relating to at least two different directions by each other, and the calculation is for converting a phase difference between two polarization data items to the axis orientation included in the representation.

13. The apparatus for processing polarization data according to claim 11, wherein the conversion unit is operable to execute a calculation for dividing polarization data items relating to at least two different directions by each other, and the calculation is for generating complex data which includes retardation and axis orientation of the sample.

14. The apparatus for processing polarization data according to claim 11, wherein the acquisition unit is operable to acquire polarization data items at different times.

15. The apparatus for processing polarization data according to claim 11, wherein the acquisition unit is operable to acquire polarization data items in different spatial positions.

16. The apparatus for processing polarization data according to claim 11, wherein the conversion unit calculates sets of Stokes vectors as the sets of polarization data items.

17. The apparatus for processing polarization data according to claim 11, wherein the averaging unit generates averaged Stokes vectors as averaged polarization data items,
wherein the apparatus further comprises a normalization unit configured to normalize the averaged Stokes vectors to give a norm of 1 in regard to the intensity of the polarization data items, and
wherein the normalization unit is implemented by the at least one processor.

18. The apparatus for processing polarization data according to claim 11, wherein the acquisition unit acquires the plurality of sets of polarization data items obtained by a polarization-sensitive optical coherence tomographic apparatus imaging the sample, which is communicably connectable.

19. The apparatus for processing polarization data according to claim 11,
wherein the generating unit generates, as the polarization-sensitive B-scan images, a retardation image and an axis orientation image by using the calculated retardation and axis orientation.

20. The apparatus for processing polarization data according to claim 11, wherein the sample is an eye.

21. A non-transitory computer readable storage medium storing a program for causing a computer to execute a method for processing polarization data of polarization-sensitive optical coherence tomography, the method comprising:
detecting light, the light being obtained by splitting combined light using a polarization beam splitter, the combined light being obtained by combining return light from a sample to be measured irradiated with measuring light and reference light corresponding to the measuring light;
acquiring a plurality of sets of polarization data items obtained from the detected light;
converting the plurality of sets of the polarization data items into a representation in vector form including information regarding retardation and axis orientation;
averaging the plurality of sets of the converted polarization data items that are expressed in the representation;
calculating retardation and axis orientation from the plurality of sets of the averaged polarization data items;
generating polarization-sensitive B-scan images of different types by using the calculated retardation and axis orientation; and
causing a display unit to display at least one of the generated polarization-sensitive B-scan images.

* * * * *